United States Patent [19]

Babej et al.

[11] 4,174,458
[45] Nov. 13, 1979

[54] NOVEL ANALOGUES OF PROSTANOIC ACIDS NOT OCCURRING IN NATURE

[75] Inventors: Milos Babej, Frankfurt am Main; Wilhelm Bartmann, Neuenhain; Gerhard Beck, Frankfurt am Main; Ulrich Lerch, Hofheim, all of Fed. Rep. of Germany

[73] Assignee: Hoechst Aktiengesellschaft, Frankfurt am Main, Fed. Rep. of Germany

[21] Appl. No.: 902,404

[22] Filed: May 3, 1978

Related U.S. Application Data

[62] Division of Ser. No. 752,433, Dec. 20, 1976, abandoned, which is a division of Ser. No. 549,651, Feb. 13, 1975.

[30] Foreign Application Priority Data

Feb. 15, 1974 [DE] Fed. Rep. of Germany ....... 2407186
Sep. 24, 1974 [DE] 09241974 .............................. 2445526

[51] Int. Cl.$^2$ .......................................... C07C 177/00
[52] U.S. Cl. .................................... 562/463; 562/472; 562/465; 560/53; 560/55
[58] Field of Search .................. 562/472, 465; 560/53, 560/55

[56] References Cited

PUBLICATIONS

Derwent Abstract 16432Y/10, BE845780.
CA 86: 189314v, 02-09-75, Upjohn.
Derwent Abstr. 79319Y/45, BE854-113 30-04-76.

Primary Examiner—Paul J. Killos
Attorney, Agent, or Firm—Curtis, Morris & Safford

[57] ABSTRACT

The present invention relates to novel not naturally occurring analogues of prostanoic acids of the formula

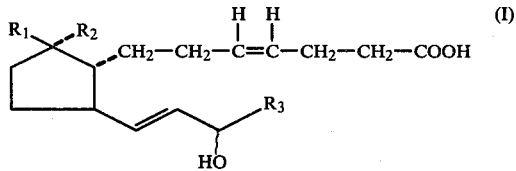

as well as a process for their preparation. The compounds of the invention have valuable pharmacological properties similar to those of the natural prostaglandins and therefore can be used as medicaments.

2 Claims, No Drawings

NOVEL ANALOGUES OF PROSTANOIC ACIDS NOT OCCURRING IN NATURE

This application is a divisional application of Ser. No. 752,433, filed Dec. 20, 1976, and now abandoned, which in turn is a divisional application of Ser. No. 549,651, filed Feb. 13, 1975.

Prostaglandins represent a group of natural substances isolated from various animal tissues. In mammals, they are responsible for a great number of physiological activities. These natural prostaglandins have a carbon structure of, in general, 20 carbon atoms and they are distinguished from each other essentially by a higher or lower content of hydroxyl groups or double bonds in the cyclopentane ring (regarding the structure and activity of prostaglandins, c.f., among others, M. F. Cuthbert "The Prostaglandins, Pharmacological and Therapeutic Advances", William Heinemann Medical Boods Ltd., London 1973).

Therefore, the synthesis of analogues of prostanoic acids not occurring in nature and which show differentiated actions of the great number of pharmacological activities of the natural prostanoic acids has become more and more important.

The present invention relates to novel analogues of prostanoic acids not occurring in nature of the formula I

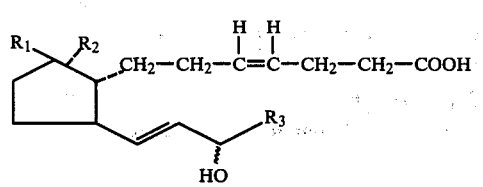

wherein
- $R_1$ and $R_2$ together represent oxygen or each of them separately hydrogen or a hydroxy group, $R_1$ and $R_2$ being different from each other,
- $R_3$ represents a saturated, straight chain or branched alkyl group of 1 to 10 carbon atoms, which itself may be substituted by an O-alkyl group of 1 to 5 alkyl C-atoms, by an O-aryl group, by an O-furyl group or by an O-benzyl group, which themselves may be substituted by one or several halogen atoms, by trifluoromethyl or alkyl groups of 1 to 3 carbon atoms or by the phenoxy group which may carry one or several halogen atoms, or a saturated cycloalkyl group of 3 to 7 ring members or an aryl or furyl group which itself may be substituted by one or several alkyl groups of 1 to 3 carbon atoms, and to their physiologically tolerated salts with organic and inorganic bases and to their esters with aliphatic, cycloaliphatic or araliphatic alcohols of 1 to 8 carbon atoms.

The present invention furthermore relates to a process for preparing the novel analogues of prostanoic acids of the general formula I which do not occur in nature, their physiologically tolerated salts with organic and inorganic bases, their esters and pharmaceutical compositions which contain these compounds as active substances.

The process of the invention essentially comprises
(a) reacting an acetal of the formula II

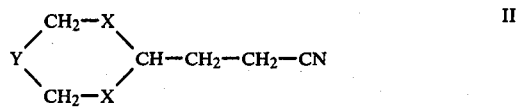

in which
X represents oxygen or sulfur, and Y represents a —$CH_2$— or

group or a simple bond,
with a Grignard compound of the formula III

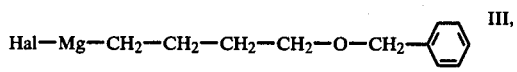

in which Hal represents chlorine or bromine, to an acetal-ketone of the formula IV

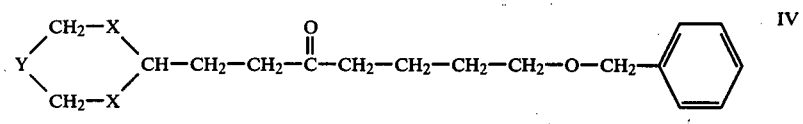

in which X and Y have the meanings given for formula II, (b) transforming the acetal-ketone of the formula IV so obtained in a manner usual for acetals or thio-acetals into the aldehyde-ketone of the formula V

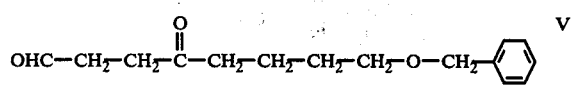

(c) subjecting the aldehyde-ketone of the formula V obtained to an aldol-condensation under acid or alkaline catalysis, whereby the unsaturated ketone of the formula VI

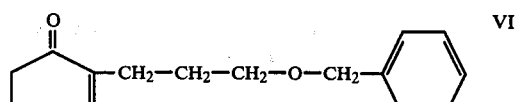

is formed, (d) reacting the unsaturated ketone of the formula VI so obtained under alkaline conditions with cyanidions, whereby the cyano-ketone of the formula VII

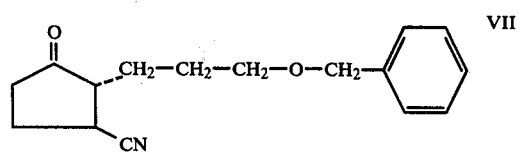

is obtained, (e) transforming the cyano-ketone of the formula VII so obtained with anhydrous alcoholic acid over the imino-ether salt of the formula VII a

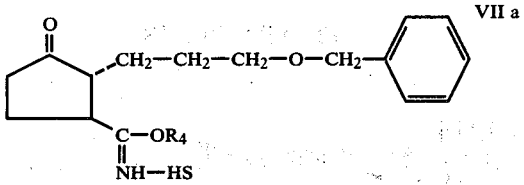

VII a in which S represents an inorganic acid radical, and R$_4$ represents lower alkyl of 1 to 5 carbon atoms, and subsequent hydrolysis into the esters of the formula VIII

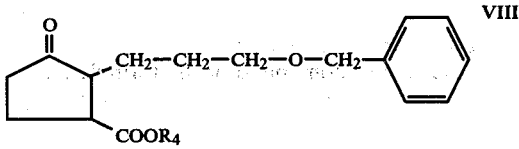

VIII in which R$_4$ has the meaning given for formula VII a, (f) hydrogenating in the presence of catalysts the ester of the formula VIII so obtained under splitting off the benzyl-ether grouping, whereby an ester-alcohol of the formula IX

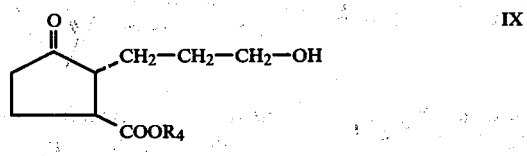

IX in which R$_4$ has the meaning given for formula VIII, is obtained, (g) oxidizing the ester-alcohol of the formula IX so obtained to an aldehyde of the formula X

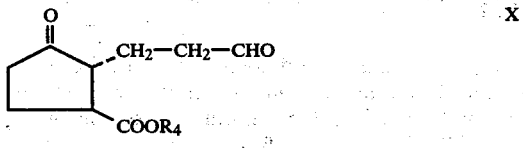

X in which R$_4$ has the meaning given for formula VIII, (h) reacting the aldehyde of the formula X so obtained selectively with a dithiol of the formula XI

HS—CH$_2$—Y$_1$—Ch$_2$—SH    XI in which Y$_1$ represents a —Ch$_2$— group or a —C(CH$_3$)$_2$ group or a simple bond, in the presence of acid catalysts to a thio-acetal of the formula XII

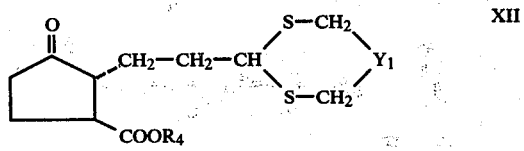

XII in which R$_4$ has the meaning given for formula X, (i) transforming the thioacetal of the formula XII so obtained by ketalization under acid catalysis with a glycol of the formula XIII

HO—Ch$_2$—Y$_2$—CH$_2$—OH    XIII in which Y$_2$ has the meaning given for Y$_1$ in formula XII, into a ketal-thioacetal of the formula XIV

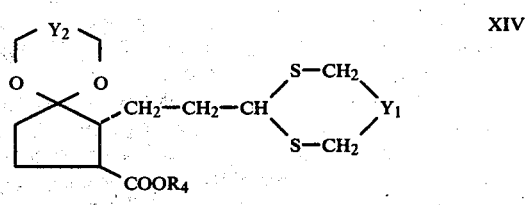

XIV in which Y$_1$ and Y$_2$ may be identical or different, and R$_4$ has the meaning given for formula X, (j) reducing the ketal-thioacetal of the formula XIV so obtained wth a complex metal hydride in aprotic solvents to an aldehyde of the formula XV

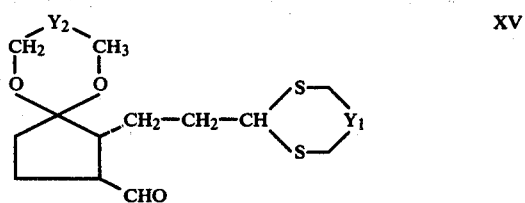

XV in which Y$_1$ and Y$_2$ have the meanings given for formula XIV, (k) reacting the aldehyde so obtained of the formula XI with a phosphonate of the formula XVI

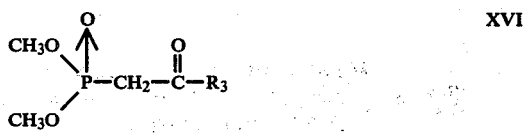

XVI in which R$_3$ has the meaning given for formula I, to an unsaturated ketone of the formule XVII

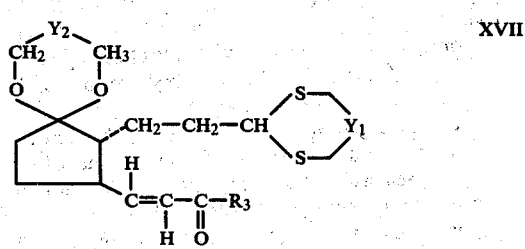

XVII in which Y$_1$ and Y$_2$ have the meanings given for formula XIV, and R$_3$ has the meaning given for formula I, (l) reducing the ketone obtained of the formula XVII with a complex metal hydride to the mixture of epimers of the alcohols of the formula XVIII

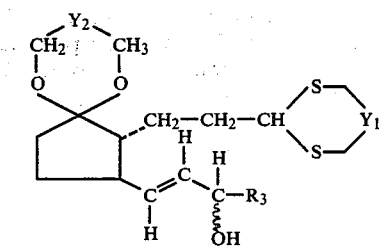

XVIII in which $Y_1$ and $Y_2$ and $R_3$ have the meanings given for formula XVII, (m) transforming the alcohol obtained of the formula XVIII in the form of the mixture of epimers or after having separated the epimers, by acid-catalyzed addition of 2,3-dihydropyrane into a tetrahydropyranyl ether of the formula XIX

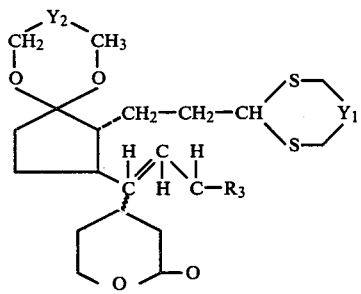

XIX in which $Y_1$ and $Y_2$ and $R_3$ have the meanings given for formula XVII, (n) transforming the ether obtained of the formula XIX by heating with a $C_1$-$C_4$-alkyl iodide in a polar aprotic solvent in the presence of an acid acceptor into an aldehyde ether of the formula XX

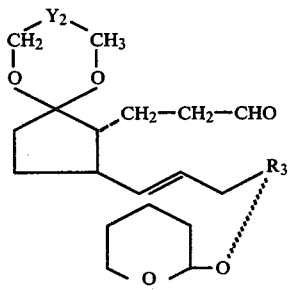

XX in which $Y_2$ and $R_3$ have the meanings given for formula XVII, (o) reacting the aldehyde ether obtained of the formula XX with the ylide from 4-carboxypropyl-triphenyl-phosphonium bromide in a solution of sodium hydride in dimethyl-sulfoxide to an acid of the formula XXI

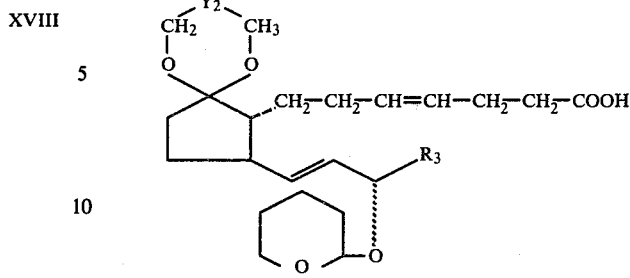

XI in which $Y_2$ and $R_3$ have the meanings given for formula XVII, (p) splitting off in the compound obtained of the formula XXI the tetrahydropyranol ether protective group by mild acid hydrolysis, whereupon an alcohol of the formula XXII

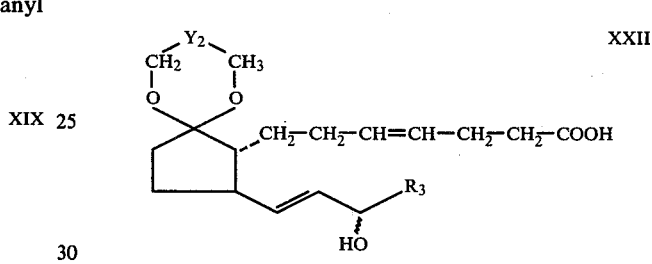

XXII in which $Y_2$ and $R_3$ have the meanings given for formula XVII, is obtained and removing the ketal grouping in the alcohol of the formula XXII either by mild acid-catalyzed hydrolysis or by transketalization in the presence of a large excess of a ketone, or effecting splitting off of both protective groups in one step by mild acid hydrolysis, and reducing optionally the compound so obtained of the formula I, in which $R_1$ and $R_2$ together represent oxygen, to a compound of the formula I, in which $R_1$ and $R_2$ represent hydrogen or hydroxyl, with a complex metal hydride, and, if desired, converting the compounds of the formula I into their physiologically tolerated salts or their esters.

Among the groups mentioned for the substituent $R_3$, there are preferred alkyl of 3 to 8 carbon atoms, cycloalkyl of 3 to 7 carbon atoms, and phenyl or phenyl which is substituted by one or several methyl groups. Furthermore, there are preferred, for $R_3$, groups of the formula —C(R')$_2$—(CH$_2$)$_n$—O—R", in which R' represents hydrogen or an alkyl group of 1 to 3 carbon atoms, in particular the methyl group, with the proviso that both R' may be identical or different, and in which n is zero or 1 and R" represents an alkyl group of 1 to 5 carbon atoms, a phenyl or benzyl group which may be substituted once or several times in the nucleus by halogen, in particular chlorine, trifluoromethyl or alkyl of 1 to 3 carbon atoms, or a diphenyl ether group, in which the benzene in terminal position may be substituted once or several times by halogen, in particular chlorine, trifluoromethyl or alkyl of 1 to 3 carbon atoms. Particularly preferred for $R_3$ are groups of the formula —C(R'-)$_2$—(CH$_2$)$_n$—O—R" in which n is zero and R" represents phenyl which is monosubstituted by chlorine or trifluoromethyl or a diphenyl ether group in which the benzene nucleus in terminal position is mono-substituted by chlorine.

The process of the invention starts with a ketone synthesis from nitriles of the general formula II.

Such nitriles may be obtained, for example by converting the 3-(2,5-dioxapentyl)-propyl-bromide, obtainable according to G. Buchi and H. Wuest, J. Org. Chem. 34, (1969), page 112, by the reaction with KCN to the 3-(2,5-dioxapentyl)-propylnitrile. This nitrile or its oxygen analogues (X = O) described by the general formula II may be reacted directly with the suitable Grignard compound of the general formula III or may be converted by acid-catalyzed trans-ketalization with thiols of the general formula XI into the sulfur analogues (X = S) of the general formula II.

In the following step, the nitriles of the general formula II (X = O or S) are reacted with Grignard compounds of the general formula III, whereupon the ketones of the general formula IV are obtained by mild acid hydrolysis. The Grignard compounds of the general formula III may be obtained in the usual manner from 4-benzyloxybutyl-chloride or -bromide in one of the usual solvents such as diethyl ether or tetrahydrofurane. In principle, also other metal-organic compounds, for example 4-benzyloxybutyl-lithium, may be used.

The components II and III are allowed to react for a period of time of from 2 to 20 hours in the presence of a protective gas. Advantageous solvents are diethylether or tetrahydrofurane, the preferred temperature are in the range of from 30° and 20° C., the reaction times in the range of from 12 to 16 hours are favorable.

The reaction product is hydrolyzed under mild acid conditions and the ketones of the general formula IV are isolated in pure form by distillation or column chromatography. However, the raw products of the general formula IV may also be used directly in the next synthesis step, the splitting off of the acetal or thioacetal protective group.

In order to obtain the aldehyde-ketone of the formula V, a usual acid ketal splitting off is carried out in the case of the oxygen acetals of the formula IV (X = O). A particularly mild mode of carrying out this step of the process of the invention comprises thoroughly mixing the solution of compounds of the general formula IV, in which X = O, in an ether, for example diisopropyl ether, at 40° to 80° C., in the presence of a protective gas, for 3 to 6 hours, with aqueous oxalic acid and, after washing to neutrality, removing the solvent by distillation. For the splitting off of thio-acetals of the general formula IV, in which X = S, the methods described in literature, for example those described by Hsin-Lan Wang Chan, Tetrahydron Lett. 1972, pages 1989–1990, are used. A preferred method of operation of the process of the invention comprises the splitting off with $CuCl_2$ and CuO as described in the Bll. Chem. Soc. Jap. 45, (1972), page 3724.

The aldehyde of the formula V can be purified by chromatography or distillation; however, it is more advantageous to use it directly without purification in the following reaction, the more so since it is obtained in high purity if the above-mentioned $CuCl_2$ - CuO method is used.

The aldehyde of the formula V is subsequently subjected to a basically catalyzed aldol condensation, whereby the unsaturated ketone of the formula VI is formed. In principle, also acid catalysts may be used in the aldol condensation. A preferred, particularly mild form of the aldol condensation consists in working, while stirring thoroughly, under exclusion of oxygen, in a two-phase system at 40° to 60° C., one phase constituting the solution of the aldehyde of the general formula V in a not-hydrolyzable, water-insoluble solvent, for example di-siopropyl ether or benzene, and the other phase consisting of aqueous 1N-sodium or potassium hydroxide solution. The unsaturated ketone of the formula VI can be purified, as already mentioned, by chromatography or distillation. It is, however, also possible to use the raw product in the further reaction.

Then, CN-ions are added in the usual manner to the ketone of the formula VI in order to obtain the cyano-ketone of the formula VII, this reaction being preferably carried out with acetocyanohydrine in a methanolic alkaline solution or with KCN in a mixture of methanol and water at room temperature. In general, the formation of cis-trans isomers must be expected in this reaction step. However, in view of the investigations carried out by D. Varech et al., Bull. Soc. Chim. 6, 1622 (1965), the more stable trans-configuration will preferably be formed under alkaline conditions.

The cyano-ketone of the general formula VII is reacted with alcoholic acid, preferably with ethanolic hydrochloric acid, over the imino-ether hydrochloride VIIa to the esters of the general formula VIII.

In this step, the imino-ether hydrochloride VIIa is obtained, after evaporation of the excess of alcohol, in the form of an oil and can be freed from by-products by extraction with weakly polar solvents, for example pentane or diethyl ether. A special mode of operation of the process of the invention consists in reacting the compounds of the general formulae V, VI and VII, each time as raw product, and removing all the by-products formed by extraction in the step VIIa.

The imino-ether hydrochloride VII a is then hydrolyzed in the usual manner to the esters of the general formula VIII, preferably by providing the aqueous solution with a layer of ether and stirring the whole at room temperature.

The ether solution then contains the esters of the general formula VIII which are purified in the usual way by distillation or by chromatographic measures.

From the esters of the general formula VIII, the ester alcohols of the general formule IX are obtained by splitting off the benzyl-ether grouping by hydrogenation, preferably in the presence of noble metal catalysts, for example 10% of palladium on animal charcoal.

The oxidation of the ester-alcohols of the general formula IX to the aldehydes of the general formula X is carried out according to one of the methods usually applied for the oxidation of primary alcohols to aldehydes. A preferred method is the oxidation with chromic anhydride in the presence of pyridine, optionally in the presence of methylene chloride as solvent, as described by Collins in Tetrahedron Lett., 3363 (1968). Another preferred method is the oxidation with chlorine in the presence of thio-anisole (Corey and Kinn, J. Org. Chem. 38 (1973) 1233)

The aldehyde of the formula X may be converted in the usual manner in its pure form, but it is of advantage to react it in its raw form in the presence of acid catalysts in inert solvents with thiols of the general formula XI to to thioacetals of the general formula XII.

A preferred mode of operation of the process of the invention consists in reacting the aldehyde of the general formula X, which is obtained with a purity of about 90%, with the equimolar quantity of a thiol of the general formula XI, for example ethylene-thioglycol, in the presence of acid catalysts, preferably boron-trifluoro-di-etherate, in the presence of an oxygenfree protective gas such as nitrogen or argon in an aprotic solvent, for example benzene or toluene, for a period of time of from 30 minutes to 5 hours at temperatures in the range of from 15° C. to 50° C. In this step, the aldehyde function in the compounds of the general formula XII is protected selectively.

The remaining keto-function in the thio-acetals of the general formula XII is then protected by ketalization with the glycols of the general formula XIII in aprotic solvents in the presence of acid catalysts, whereby the ketal-thio-acetals of the general formula XIV are obtained. A particularly preferred method is the ketalization of XII with glycols of the general formula XIII, for example ethylene-glycol or neopentyl-glycol, in which the reaction components are heated for 3 to 5 hours in benzene or toluene on a water-separator, whereby the ketal-thioacetals of the general formula XIV are obtained.

The compounds of the formulae IX, X, XII and XIV each may be converted into their pure forms; however, in the process of the invention it is of advantage to further process the compounds of the general formulae IX, X and XII, which are obtained in high yields in the respective reaction steps as crude products and to purify the compounds of the general formula XIV in the usual manner, preferably by column chromatography.

In the ketal-thioacetals of the general formula XIV, the ester functions are reduced with a complex metal hydride, preferably di-isobutyl-aluminum hydride, in an inert solvent such as toluene, at temperatures below 0° C., preferably at −40° to −80° C., to the aldehydes of the general formula XV.

The aldehydes of the general formula XV are then reacted according to Horner, Emmons and Wittig with the phosphonic acid esters of the general formula XVI to the unsaturated ketones of the general formula XVII, a preferred mode of carrying out the reaction consisting in preparing the sodium salt of the phosphonic acid esters of the general formula XVI with sodium hydride in glycol-dimethylether and subsequently adding the aldehydes of the general formula XV and allowing the whole to react for 2 to 6 hours. The phosphonic acid esters of the general formula XVI are prepared according to methods known in literature (c.f. for example Corey, J. Am. Chem. Soc. 88, 5654 (1966)).

The alcohols of the general formula XVIII are obtained in the form of their epimeric mixtures, by reducing the ketones of the general formula XVII with a complex metal hydride, preferably an alkali metal boramate. The alcohols of the general formula XVIII are particularly suitable for a separation of the epimers, but the further reaction may also be carried out with the epimeric mixture and the separation of the epimers may be effected at the stage of the final products.

The addition of dihydropyrane to the tetrahydropyranyl ether of the general formula XI is carried out in an ether or benzene solution of the alcohols of the general formula XVIII, in the presence of the usual acid catalysts, for example p-toluene-sulfonic acid. In general, it is advantageous to purify at this stage by chromatography the tetrahydropyranyl ether obtained of the general formula XVIII.

Owing to the preparative difficulties involved, the liberation of aldehydes and ketones from thio-acetals or thio-ketals has been the subject of many publications (c.f. among others Chang in Tetrahydron Letters No. 19, page 1989 (1972)). In particular, the preparation of the relatively sensitive aliphatic aldehydes is very difficult, the more so if particularly unstable protective groups, for example the tetrahydropyranyl ether group, are present in the same molecule. It is surprising that upon addition of acid-binding agents, preferably calcium carbonate, to a solution of the thioacetals of the general formula XIX in polar aprotic solvents, preferably dimethylformamide or acetone, the aldehydes of the general formula XX are formed in practically quantitative yield under maintenance of the tetrahydropyranyl protective group after heating for 1 to 5 hours to a temperature in the range of from 30° to 70° C., preferably 50° C., with $C_1$–$C_4$-alkyl iodide, preferably methyl iodide.

The aldehyde ethers so prepared of the general formula XX may be reacted without purification to the carboxylic acids of the general formula XXI. The preferred form of operation using the Wittig reaction is effected in accordance with the method described in J. Org. Chem. 28, 1128 (1963).

The splitting off of the ether protective groups is effected by mild acid hydrolysis of the tetrahydropyranyl ether grouping, preferably in a 2% aqueous alcoholic oxalic acid solution at 20° to 50° C. or by heating for 1 to 2 hours in 60 to 70% acetic acid to 50° C., whereby the carboxylic acids of the general formula XXII are obtained.

The last step of the synthesis of this invention comprises the mild acid hydrolysis of the ketal grouping of the compounds of the formula XXII to compounds of the general formula I in which $R_1$ and $R_2$ together represent oxygen. Another method for the ketal separation comprises the trans-ketalization of XXII to I in which $R_1$ and $R_2$ together represent oxygen, in the presence of a large excess of a ketone, preferably acetone, in the presence of acid catalysts such as p-toluene-sulfonic acid.

However, in a preferred method of the process of the invention, both protective groups in the carboxylic acids of the formula XXI may be split off in one step by acid hydrolysis, for which purpose 10% aqueous oxalic acid has proved particularly advantageous. Thereby, the compounds of the general formula I are obtained in which $R_1$ and $R_2$ together represent oxygen.

The reduction to compounds of the formula I in which $R_1$ and $R_2$ represent hydrogen or hydroxyl is carried out with a complex metal hydride, preferably with a metal boranate, for example sodium boron hydride, in an aqueous-alcoholic solution. A mixture of the $9\alpha,\beta$-epimeric alcohols is obtained. The epimers can be separated in the usual manner, for example by thin-layer chromatography or by partition chromatography.

If no separation of the epimers at the stage of the alcohols of the general formula XVIII has been effected, it is possible to subject the compounds of the general formula I in which $R_1$ and $R_2$ represent oxygen to an epimer dissociation of the alcohols in 15-position (15-OH according to the prostaglandin nomenclature (cf. Andersen, Ann. New Yor. Acad. Sci. Acad. Sci., Vol. 180, page 14) corresponding to 3-OH of the IUPAC nomenclature).

Furthermore, a racemate resolution may be carried out at the stage of the acids of the general XXI or of the formula I in the usual manner by salt formation with optically active bases.

The compounds off the formulae IV, V, VI, VII, VIII, IX, X, XII, XIV, XV, XVII, SVIII, XIX, XX, XXI and XXII are valuable intermediate products for the synthesis of the compounds of the formula I.

The compounds of the invention are distinguished by spasmogenic as well as spasmolytic, in particular bronchodilating and blood-pressure lowering properties. They are furthermore therapeutically active in the case of gastro-intestinal disorders and have an anti-fertility action. In comparison to the natural prostaglandins E, F and E, they have an essentially better stability. They may, therefore, be used as medicaments.

In this respect it is surprising that the compounds of the formula I which are epimeric with regard to the 15-OH group possess the mentioned pharmacological properties at about the same degree.

The compounds of the invention may be used as free acids, in the form of their physiologically tolerated salts or of their esters with aliphatic, cycloaliphatic or araliphatic alcohols of 1 to 8 carbon atoms. As salts, there may be used, for example the benzylammonium, triethanolammonium or morpholine salts, in particular the tris-(hydroxymethyl)-aminomethane salt, as well as the alkali metal salts such as the Na- and K-salts, as esters there are preferably used the esters of lower saturated aliphatic alcohols such as the methyl, ethyl, propyl, isopropyl, butyl or pentyl ester, and the benzyl ester.

The acids, salts or esters may be administered in the form of their aqueous solutions or suspensions or even as solutions in pharmacologically tolerated organic solvents, for example mono- or polyhydric alcohols, dimethyl-sulfoxide or dimethyl-formamide, or also together with pharmacologically tolerated polymeric carrier substances, for example polyvinyl-pyrrolidone.

The pharmaceutical compositions may be the usual galenic infusion or injection solutions, or tablets; preferably, however, there are used locally applicable compositions such as creams, emulsions, suppositories or aerosols.

The compounds may be used as such alone or together with other pharmacologically active substances, for example diuretic agents or anti-diabetic agents.

Bronchodilating active medicaments with a surprisingly strong action are obtained by mixing the compounds of 7-[2-(3-hydroxy-3-pentyl-trans-1-propenyl)-5-oxo-cyclopentyl]-cis-4-heptenoic acid, epimeric with regard to the 15-OH-group, either in the form of a free acid or in the form of their physiologically tolerated inorganic or organic salts or of their esters of aliphtic, cycloaliphatic or araliphatic alcohols of 1 to 8 carbon atoms, at a weight proportion of 0.75 to 1 to 1.25 to 1; such mixtures have the greatest activity when applied in the form of an aerosol.

Surprisingly, such mixtures show an activity which is several times higher than the activities of the individual isomers. Particularly advantageous is a mixture of the isomers in a weight proportion of 1:1.

In the medicinal compositions of the invention, the isomers are likewise used in the form of the free acids, in the form of the Na- or K-salts or of salts with organic bases such as benzyl-ammonium, triethanolammonium or morpholine salts, in particular of the tris-(hydroxymethyl)-aminomethane salt or in the form of the esters of lower, saturated, straight-chain or branched aliphatic alcohols such as the methyl, ethyl, propyl, isopropyl, butyl or pentyl ester or benzyl ester.

Particularly preferred are corresponding mixtures of the isomeric free acids and of the methyl, ethyl, propyl and isopropyl esters of the mentioned acids.

For administration in aerosol form, the mixture of the invention may be dissolved in the usual physiologically tolerated solvents which are not irritating with regard to taste, for example water or ethanol, or suspended, for example in lower alkyl esters of higher fatty acids, for example the myristic acid isopropyl ester, if desired with the addition of surface-active agents as stabilizers, for example sorbitane- or pentaerythritol fatty acid ester, and filled, together with one of the usual inert propellant gases in aerosol containers. However, the mentioned compositions may also be administered by means of a conventional atomizer with the aid of compressed air.

The following dosage units or daily doses may be administered for the various possible indications:

| Bronchodilating action (as aerosol): | |
|---|---|
| Dosage unit: 0.1–1000/µg | |
| preferred: 1–200µg | (per single spray output) |
| Daily dose: 0.1–10 mg | |
| Blood-pressure-lowering action: | |
| Dosage unit: 1–1000 µg | |
| preferred: 1–100 µg | parenterally (i.v.) |
| Daily dose: 1–10 mg | |
| Dosage unit: 0.5–1100 µg | |
| preferred: 1–500 µg | orally |
| Daily dose: 1 mg–10 mg | |

The doses in the administration against gastro-intestinal disorders corresond to those indicated for the application as blood-pressure-lowering agents.

The following Examples illustrate the invention.

EXAMPLES

Starting materials 3-(2,5-dioxapentyl)-propyl bromide was prepared according to G. Büchi and H. Wuest (J. Org. Chem. 34 (1969) page 1122) and heated in a manner analogous to that described by Wohl, Chem. Ber. 39 (1906), page 1952, for 3 hours under reflux in a mixture of 60 parts of ethyl alcohol and 40 parts of $H_2O$ with 2 molar equivalents of KCN in the presence of catalytical amounts of potassium iodide. The 3-(2,5-dioxapentyl)-propylcyanide (B.p.$_{0.6}$ mm 68°–69° C.) was heated under reflux in benzene with ethylene-thioglycol in the presence of boron-trifluoride-etherate, whereupon, after the usual working up, 3-(2,5-dithiapentyl)-propylcyanide having a B.p.$_{0.5}$ $mm$ of 124°–126° C. was obtained.

4-Benzyloxybutanol was obtained according to the method described by Butler, Reufrew and Clapp (Am. Soc. 60 (1938) 1472) and transformed according to Bennett and Hock, J. Chem. Soc. (Lond.) 1927, page 476, into the 4-benzyloxybutyl-chloride.

EXAMPLE 1

The Grignard compound was prepared by a 5 hours' heating of [0.103 mole]=2.5 g of Mg and [0.101 mole]=20 g of 4-benzyloxybutyl chloride in 50 ml of diethyl ether.

To this Grignard solution, there was added dropwise the solution of 12 g=[0.076 mole] of 3-(2,5-dithiapentyl)-propylcyanide in 50 ml of diethyl ether and the whole was heated for 18 hours under argon and under reflux. After cooling, 200 ml of methylene chloride and ice water were added, the mixture was acidified to pH 1 by means of HCl and stirred for 15 minutes. The organic phase was separated, washed with water and concentrated. The residue was dissolved in 200 ml of acetone and 50 ml of methanol and stirred with 25 ml of 2N-HCl for 4 hours at room temperature. The solvent was concentrated under reduced pressure, the residue was dissolved in methylene chloride, washed once with a 2N-sodium carbonate solution and twice with water, dried over Mg SO$_4$ and concentrated. The residue was distilled under reduced pressure. B.p.$_{0.3\,mm}$ 205°–207° C.

EXAMPLE 2

7-Benzyloxy-3-oxoheptanal 0.135 mole=44 g of 7-benzyloxy-1-(2,5-dithiapentyl)-heptane-3-one were heated for 1 hour under nitrogen and under reflux in 1 liter of acetone with [0.275 mole]=47 g of CuCl$_2$ . 2 H$_2$O and [0.57 mole]=44 g of CuO, the copper salts were filtered off and the filtrate was concentrated under reduced pressure. The residue was dissolved in ether, washed twice with 2N- HCl and thrice with water, dried and the solvent was removed by distillation under reduced pressure. The residue was distilled under reduced pressure. B.p.$_{0.5\,mm}$ 185°–192° C.

EXAMPLE 3

2-(3-Benzyloxypropyl)-2-cyclopentanone 30.8 g of crude 7-benzyloxy-3-oxoheptanal were dissolved in 100 ml of di-isopropyl ether and well mixed with 500 ml of 1N-sodium hydroxide solution at 50° C. under nitrogen with the aid of a vibromixer. The organic phase was separated, the aqueous phase was extracted with 200 ml of ether and the combined ether extracts were washed with water, dried, concentrated and distilled under reduced pressure. B.p.$_{0.5\,mm}$ 175°–180° C.

EXAMPLE 4

2-(3-Benzyloxypropyl)-3-cyano-cyclopentanone 47.8 g=[0.208 mole] of 2-(3-benzyloxypropyl)-2-cyclopentanone were dissolved in 200 ml of methanol, 41.5 g=[0.64 mole] of KCN were added and then 15 g=]0.25 mole] of glacial acetic acid in 25 ml of methanol were added dropwise within one hour. After having stirred for 1 hour, 4 g=[0.066 mole] of glacial acetic acid were again added and the whole was stirred for a further hour. After this time, no starting material could be detected in the thin-layer chromatogram. 100 ml of 2N-NaOH and 900 ml of ice-water were added and the mixture was extracted thrice with 200 ml of diethyl ether, the combined ether extracts were washed until neutral, dried and the solvent was removed by distillation under reduced pressure. The residue was distilled. B.p.$_{0.5\,mm}$ 210°–215° C.

EXAMPLE 5

3-Ethoxycarbonyl-2-(3-benzyloxy-propyl)-cyclopentanone

[0.02 mole]=5.1 g of 2-(3-benzyloxypropyl)-3-cyanocyclopentanone were dissolved in 25 ml of absolute benzene with [0.022 mole]=1 g of absolute ethyl alcohol while stirring, at 20° C., and HCl gas was introduced slowly within 4 hours. The reaction mixture was allowed to stand for 16 hours at room temperature. The solvent was removed under reduced pressure and the residue was stirred thrice with each time 75 ml of absolute di-ethyl ether and these ether extracts were rejected.

The oily residue was dissolved in 20 ml of water, provided with a layer of 100 ml of di-ethyl ether and stirred for 30 minutes at room temperature, the organic phase was separated and the aqueous phase was extracted with 200 ml of di-ethyl ether. The combined ether extracts were washed with 2N-sodium carbonate solution and water, dried and the solvent was removed under reduced pressure. An oil was obtained. An analytically pure sample was eluted by chromatography on silica gel with a mixture of cyclohexane and glacial acetic acid in a proportion of 9:1 and showed the following spectroscopic data:

N.M.R. 7.3 ppm singulett 5 H,/4.2 (c) ppm 4,4 ppm singulett 2 H,/quartett 2H.

EXAMPLE 6

3-Ethoxycarbonyl-2-(3-oxypropyl)-cyclopentanone 5 g of 3-ethoxycarbonyl-2-(3-benzyloxy-propyl)-cyclopentanone were hydrogenated in 50 ml of 80% acetic acid with 1 g of palladium black at room temperature and a pressure of 50 atmospheres gauge. The reaction mixture was combined with 100 ml of water and 100 ml of methylene chloride, the catalyst was filtered off, the whole was combined with an aqueous soda solution until pH 8 to 9, the methylene chloride was separated, the remainder was washed, dried and distilled under reduced pressure. The oily residue was heated for 1 hour to 50° C. at 0.02 mm Hg.

I.R. 3500 cm$^{-1}$.

EXAMPLE 7

3-(2-Ethoxycarbonyl-5-oxo-cyclopentyl)-propionaldehyde 3.07 g=[0.014 mole] of 3-ethoxycarbonyl-2-(3-oxypropyl)-cyclopentanone were dissolved in 3 ml of methylene chloride and added dropwise to the oxydation reagent of 11.95 g of CrO$_3$ and 19.15 g of pyridine in 300 ml of methylene chloride at 0° C. After stirring for 35 minutes at 0° C., 61.8 g of sodium hydrogene-sulfate-monohydrate in solid form were added and the whole was further stirred for 30 minutes at 0° C. The suspension was filtered through a clarifying filter and the filter residue was washed six times with each time 50 ml of methylene chloride. The combined methylene chloride filtrates were dried over MgSO$_4$ and concentrated. An oil was obtained.

I.R. no OH-band at 3500 cm$^{-1}$, wide carbonyl band at 1730–1740 cm$^{-1}$.

EXAMPLE 8

3-(2-Ethoxycarbonyl-5-oxo-cyclopentyl)-propionaldehyde-ethylene-thioacetal 3 g=[0.014 mole] of oily 3-(2-ethoxycarbonyl-5-oxo-cyclopentyl)-propionaldehyde were stirred for 3 hours at room temperature with 1.29 g=[0.0137 mole] of ethylene thioglycol, 0.5 ml of boron-trifluoro-di-etherate and 50 ml of anhydrous benzene, diluted with 150 ml of ether and washed with ice-cold 1N-NaOH and water. The mixture was dried over sodium sulfate and the solvent was evaporated under reduced pressure. An oil was obtained.

I.R.=1740 cm$^{-1}$.

EXAMPLE 9 a

7-[(1,3-dithia-2-cyclopentyl)-ethyl]-3,3-dimethyl-1,5-dioxaspiro-[5,4]-dec-8-yl-carboxylic acid ethyl ester 3.35 g=[0.0116 mole] of 3-(2-ethoxycarbonyl-5-oxocyclo-pentyl)-propionaldehyde-ethylene-thioacetal were heated for 3 hours on a water separator under reflux with 2.1 g=[0.02 mole] of 2,2-dimethyl-1,3-propane-diol, 0.2 g of p-toluenesulfonic acid and 50 ml of benzene. After cooling, the reaction mixture was diluted with ether, washed with ice-cold 2N-sodium carbonate solution, dried over Na$_2$SO$_4$ and concentrated. From the oil that had formed, there was obtained an analytically pure product by chromatography on silica gel and elution with cyclohexane/ethyl acetate in a ratio of 95:5.

N.M.R. 4.2 ppm (c)-quartett 2H; 3.5 ppm singulett 4H.

EXAMPLE 9 b

In a manner analogous to that described above, there was obtained with ethylene glycol the 6-[(1,3-dithia-2-cyclopentyl)-ethyl]-1,4-dioxaspiro-[4,4]-none-7-yl-carboxylic acid ether ester.

N.M.R. 3.8–45 ppm singulett+multiplett 7H; 3.2 ppm singulett 4H.

EXAMPLE 10

7-[(1,3-dithia-2-cyclopentyl)-ethyl]-3,3-dimethyl-1,5-dioxaspiro-[5,4]-dec-8-yl-aldehyde 1.3 g=[3.5 mmoles] of 7-[(1,3-dithia-2-cyclopentyl)-ethyl]-3,3-dimethyl-1,5-dioxaspiron-[5,4]-dec-8-yl-carboxylic acid ethyl ester were dissolved in 50 ml of absolute toluene, then 0.7 ml=[3.85 mmoles] of di-isobutyl-aluminium-hydride in 10 ml of absolute toluene were added dropwise within 20 minutes at −70° C. and the whole was stirred for 2 hours at −70° C. 1 ml of methanol and 0.5 ml of glacial acetic acid were added dropwise, then 20 ml of water were added and finally 50 ml of diethyl ether were added. The turbid solution was filtered through a clarifying filter and the residue was washed with ether. The ether phase was washed with a solution of sodium bicarbonate, dried and concentrated under reduced pressure. The oil that had formed showed the following spectral data:

N.M.R. 9.35 ppm dublett 1H; 4.4 ppm triplett 1 H; 3.5 ppm singulett 4 H; 3.2 ppm singulett 4H.

EXAMPLE 11 a

1-[4-[(1,3-dithia-2-cyclopentyl)-ethyl]-3,3-dimethyl-1,5-dioxaspiro-[5,4]-dec-8-yl]-trans-1-octene-3-one 0.1 g=[3.3 mmoles] of 80% sodium hydride were stirred for 15 minutes at room temperature in 25 ml of glycol-dimethyl ether and then 0.89 g=[4 mmoles] of dimethyl-2-oxo-heptylphosphonate were added dropwise. After a 25 minutes' stirring, a white emulsion had formed. To this emulsion, a solution of 1.06 g=[3.2 mmoles] of 7-[1,3-dithia-2-cyclopentyl)-ethyl]-3,3-dimethyl-1,5-dioxaspiro[5,4]-dec-8-yl-aldehyde was added dropwise and the whole was stirred for 2½ hours at room temperature. After this time, the solution was only weakly turbid. Some drops of glacial acetic acid and 2 spatula points of charcoal were added and the whole was filtered. The filtrate was concentrated under reduced pressure, whereupon a light oil was obtained. Chromatography on silica gel and elution with cyclohexane/ethyl acetate 95:5 and 90:10 yielded the analytically pure sample.

N.M.R. 5.8–6.8 ppm multiplett 2 H; 4.4 ppm triplett 1 H; 3.5 ppm singulett 4 H; 3.2 ppm singulett 4 H.

EXAMPLE 11 b

In analogous manner, there was prepared by the reaction with dimethyl-2-oxo-nonylphosphate, the 1-[7-(1,3-dithia-2-cyclopentyl)-3,3-dimethyl-1,5-dioxaspiro[5,4]-dec-8yl]-trans-1-decene-3-one.

EXAMPLE 11 c

In analogous manner, there was prepared by the reaction with dimethyl-2-cyclohexyl-2-oxo-ethyl-phosphonate, the 1-[7-[1,3-dithia-2-cyclopentyl)-ethyl]-3,3-dimethyl-1,5-dioxaspiro[5,4]-dec-8-yl]-3-cyclohexyl-trans-1-propene-3-one.

EXAMPLE 11 d

In analogous manner, there was prepared by the reaction with dimethyl-2-(1,1-dimethyl-3-oxa-pentyl)-2-oxo-pentyl-phosphonate, the 1-[7-[(1,3-dithia-2-cyclopentyl)-ethyl]-3,3-dimethyl-1,5-dioxaspiro[5,4]dec-8-yl]-3-(1,1-dimethyl-3-oxa-pentyl)-trans-1-propene-3-one.

EXAMPLE 11 e

In analogous manner, there was prepared by the reaction with dimethyl-2-cycloheptyl-2-oxo-ethyl-phosphonate, the 1-[7-[(1,3-dithia-2-cyclopentyl)-ethyl]-3,3-dimethyl-1,5-dioxaspiro[5,4]-dec-8-yl]-3-cycloheptyl-trans-1-propene-3-one.

N.M.R. 5.8–6.8 ppm multiplett 2 H

EXAMPLE 11 f

In analogous manner, there was prepared by the reaction with dimethyl-2-oxo-pentylphosphonate, the 1-[7-[(1,3-dithia-2-cyclopentyl)-ethyl]-3,3-dimethyl-1,5-dioxaspiro[5,4]-dec-8-yl]-trans-1-hexene-3-one.

N.M.R. 5,8–6,8 ppm multiplett 2 H

EXAMPLE 11 g

In analogous manner, there was prepared by the reaction with dimethyl-2-[1-methyl-1-[p-(p-chloro-phenoxy)-phenoxy]-methyl]-2-oxo-ethyl-phosphonate, the 1-[6-[(1,3-dithia-2-cyclopentyl)-ethyl]-1,4-dioxaspiro[4,4]-none-7-yl]-3-[1-methyl-1-[p-(p-chloro-phenoxy)-phenoxy]methyl]-trans-1-propene-3-one.

N.M.R. 6.3–7.4 ppm multiplett 10 H; 4.5 ppm (c) multiplett 1 H; 3.9 ppm singulett 4 H; 3.15 ppm singulett 4 H.

EXAMPLE 11 h

In analogous manner, there was prepared by the reaction with dimethyl-2-[1,1-dimethyl-1-[p-(p-chloro-phenoxy)-phenoxy]-methyl]-2-oxo-ethyl-phosphonate, the 1-[6-[(1,3-dithia-2-cyclopentyl)-ethyl]-1,4-dioxaspiron[4,4]none-7-yl]-3-[1,1-dimethyl-1-[p-(p-chloro-phenoxy)-phenoxy]-methyl]-trans-1-propene-3-one.

N.M.R. 6.8–7.4 ppm multiplett 10 H; 4.5 ppm multiplett 1 H; 3.9 ppm singulett 4 H; 3.15 ppm singulett 4 H.

EXAMPLE 11 i

In analogous manner, there was prepared by the reaction with dimethyl-2-phenoxymethyl-2-oxo-ethyl-phosphonate, the 1-[6-[(1,3-dithia-2-cyclopentyl)-ethyl]-1,4-dioxaspiro[4,4]none-7-yl]-3-phenoxymethyl-trans-1-propene-3-one.

N.M.R. 6.8–7.5 ppm multiplett 5H.

EXAMPLE 11 j

In analogous manner, there was prepared by the reaction with dimethyl-2-(4-fluorophenoxy)-methyl-2-oxo-ethyl-phosphonate, the 1-[6-[(1,3-dithia-2-cyclopentyl)-ethyl]-1,4-dioxaspiro[4,4]-none-7-yl]3-(4-fluorophenoxy)-methyl-trans-1-propene-3-one.

N.M.R. 6.9–7.3 ppm multiplett 4 H.

EXAMPLE 11 k

In analogous manner, there was prepared by the reaction with dimethyl-2-(3-chlorophenoxy)-methyl-2-oxo-ethylphosphonate, the 1-[6-[(1,3-dithia-2-cyclopentyl)-ethyl]-1,4-dioxaspiro[4,4]-none-7-yl]-3-(3-chlorophenoxy)-methyl-trans-1-propene-3-one.

N.M.R. 6.7–7.5 ppm multiplett 4 H.

EXAMPLE 11 l

In analogous manner, there was prepared by the reaction with dimethyl-2-(3-trifluoromethyl-phenoxy)-methyl-2-oxo-ethyl-phosphonate, the 1-[6-[(1,3-dithia-2-cyclopentyl)-ethyl]-1,4-dioxaspiro[4,4]-none-7-yl]-3-(3-trifluoromethylphenoxy)methyl-1-trans-1-propene-3-one.

N.M.R. 7.0–7.6 ppm multiplett 4 H.

EXAMPLE 11 m

In analogous manner, there was prepared by the reaction with dimethyl-2-isobutyl-2-oxo-ethyl-phosphonate, the 1-[6-[(1,3-dithia-2-cyclopentyl)-ethyl]-1,4-dioxaspiro[4,4]none-7-yl]-3-isobutyl-trans-1-propene-3-one.

N.M.R. 5.9–7 ppm multiplett 2 H; 4.5 ppm multiplett 1 H; 3.95 ppm singulett 4 H; 3.2 ppm singulett 4 H.

EXAMPLE 11 n

In analogous manner, there was prepared by the reaction with dimethyl-2-(1,1-dimethylpentyl)-2-oxo-ethyl-phosphonate, the 1-[6-[(1,3-dithia-2-cyclopentyl)-ethyl]-1,4-dioxaspiro[4,4]none-7-yl]-3-(1,1-dimethylpentyl)-trans-propene-3-one.

EXAMPLE 12 a

1-[7-[(1,3-dithia-2-cyclopentyl)-ethyl]-3,3-dimethyl-1,5-dioxaspiro[5,4]-dec-8-yl]-trans-1-octene-3-ol 0.12 g of NaBH$_4$ [3.2 mmoles] were dissolved in 1 ml of H$_2$O + 10 ml of CH$_3$OH, cooled to 0° C. and 1.28 g (3 mmoles) of 1-[7-[(1,3-dithia-2-cyclopentyl)-ethyl]-3,3-dimethyl-1,5-dioxaspiron[5,4]-dec-8-yl]-tran-1-octene-3-one in 15 ml of methanol were added dropwise; the whole was stirred for 1 hour at room temperature. The solution was neutralized with glacial acetic acid, concentrated under reduced pressure and the residue was dissolved in diethyl ether and washed with water. After removal of the ether by evaporation, an oil remained which showed the following spectral data:

I.R. 3500 cm$^{-1}$; no carbonyl band.
N.M.R. 5.3–5.7 ppm multiplett 2 H.

EXAMPLE 12 b

In analogous manner there was prepared from 1-[7-[(1,3-dithia-2-cyclopentyl)-ethyl]-3,3-dimethyl-1,5-dioxaspiro[5,4]-dec-8-yl]-trans-1-decene-3-one, the 1-[7-(1,3-dithia-2-cyclopentyl)-ethyl]-3,3-dimethyl-1,5-dioxaspiro[5,4]-dec-8-yl]-trans-1-decene-3-ol.

I.R. 3500 cm$^{-1}$.
N.M.R. 5.3–5.7 ppm multiplett 2 H.

EXAMPLE 12 c

Analogously, from 1-[7-[(1,3-dithia-2-cyclopentyl)-ethyl]-3,3-dimethyl-1,5-dioxaspiro[5,4]-dec-8-yl]-3-cyclohexyl-trans-1-propenone-5-one, the 1-[7-[(1,3-dithia-2-cyclopentyl)-ethyl]-3,3-dimethyl-1,5-dioxaspiro[5,4]-dec-8-yl]-3-cyclohexyl-trans-1-propene-3-ol.

I.R. 3500 cm$^{-1}$.
N.M.R. 5.3–5.7 ppm multiplett 2 H.

EXAMPLE 12 d

From 1-[7-[(1,3-dithia-2-cyclopentyl)-ethyl]-3,3-dimethyl-1,5-dioxaspiro[5,4]-dec-8-yl]-3-(1,1-dimethyl-3-oxapentyl)-trans-1-propene-3-one, the 1-[7-[(1,3-dithia-2-cyclopentyl)-ethyl]-3,3-dimethyl-1,5-dixoaspiro[5,4]-dec-8-yl]-3-(1,1-dimethyl-3-oxapentyl)-trans-1-propene-3-ol.

I.R. 3500 cm$^{-1}$.
N.M.R. 5.3–5.7 ppm multiplett 2 H.

EXAMPLE 12 e

From 1-[7-[(1,3-dithia-2-cyclopentyl)-ethyl]-3,3-dimethyl-1,5-dioxaspiro[5,4]-dec-8-yl]-3-cycloheptyl-trans-1-propene-3-one, the 1-[7-[(1,3-dithia-2-cyclopentyl)-ethyl]-3,3-dimethyl-1,5-dioxaspiro[5,4]-dec-8-yl]-3-cycloheptyl-trans-1-propene-3-ol.

I.R. 3500 cm$^{-1}$.
N.M.R. 5.3–5.7 ppm multiplett 2 H.

EXAMPLE 12 f

In a manner analogous to that described in Example 12 a, there was prepared from 1-[7-[(1,3-dithia-2-cyclopentyl)-ethyl]-3,3-dimethyl-1,5-dioxaspiro[5,4]-dec-8-yl]-trans-1-hexene-3-one, the 1-[7-[(1,3-dithia-2-cyclopentyl)-ethyl]-3,3-dimethyl-1,5-dioxaspiro[5,4]-dec-8-yl]-trans-1-hexene-3-ol.

I.R. 3500 cm$^{-1}$.
N.M.R. 5.3–5.7 ppm multiplett 2 H.

EXAMPLE 12 g

In a manner analogous to that described in Example 12 a, there was prepared from 1-[6-[(1,3-dithia-2-cyclopentyl)-ethyl]-1,4-dioxaspiro[4,4]-none-7-yl]-3-[1-methyl-1-[p-(p-chlorophenoxy)-phenoxy]methyl]-trans-1-propene-3-one, the 1-[6-[(1,3-dithia-2-cyclopentyl)-ethyl]-1,4-dioxaspiro[4,4]-none-7-yl]-3[1-methyl-1-[p-(p-chlorophenoxy)-phenoxy]methyl]-trans-1-propene-3-ol.

I.R. 3500 cm$^{-1}$.
N.M.R. 5.3–5.7 ppm multiplett 2 H.

EXAMPLE 12 h

In a manner analogous to that described in Example 12 a, there was prepared from 1-[6-[(1,3-dithia-2-cyclopentyl)-ethyl]-1,4-dioxaspiro[4,4]-none-7-yl]-3-[1,1-dimethyl-1-[p-(p-clorophenoxy)-phenoxy]-methyl]-trans-1-propene-3-one, the 1-[6-[(1,3-dithia-2-cyclopentyl)-ethyl]-1,4-dioxaspiro[4,4]-none-7-yl]-3-[1,1-dimethyl-1-[p-(p-chlorophenoxy)-phenoxy]-methyl]-trans-1-propene-3-ol.

I.R. 3500 cm$^{-1}$.
N.M.R. 5.3–5.7 ppm multiplett 2 H.

EXAMPLE 12 i

In a manner analogous to that described in Example 12 a, there was prepared from 1-[6-[(1,3-dithia-2-cyclopentyl)-ethyl]-1,4-dioxaspiro[4,4]-none-7-yl]-3-phenoxymethyl-trans-1-propene-3-one, the 1-[6-[(1,3-dithia-2-cyclopentyl)-ethyl]-1,4-dioxaspiro[4,4]-none-7-yl]-3-phenoxymethyl-1-trans-propene-3-ol.

I.R. 3500 cm$^{-1}$.
N.M.R. 5.3–5.7 ppm multiplet 2 H.

EXAMPLE 12 j

In a manner analogous to that described in Example 12 a, there was prepared from 1-[6-[(1,3-dithia-2-cyclopentyl)-ethyl]-1,4-dioxaspiro[4,4]-none-7-yl]-3-(-4- fluorophenoxy)-methyl-trans-1-propene-3-one, the 1-[6-[(1,3-dithia-2-cyclopentyl)-ethyl]-1,4-dioxaspiro[4,4]-none-7-yl]-3-(4-fluorophenoxy)-methyl-trans-1-propene-3-ol.

I.R. 3500 cm$^{-1}$.
N.M.R. 5.3–5.7 multiplett 2 H.

EXAMPLE 12 k

In a manner analogous to that described in Example 12 a, there was prepared from 1-[6-[(1,3-dithia-2-cyclopentyl)-ethyl]-1,4-dioxaspiro[4,4]-none-7-yl]-3-(3-chlorophenoxy)-methyl]-trans-1-propene-3-one, the 1-[6-[(1,3-dithia-2-cyclopentyl)-ethyl]-1,4-dioxaspiro[4,4]-none-7-yl]-3-[(3-chlorophenoxy)-methyl]-trans-1-propene-3-ol.

I.R. 3500 cm$^{-1}$.
N.M.R. 5.3–5.7 ppm multiplett 2 H.

EXAMPLE 12 l

In a manner analogous to that described in Example 12 a, there was prepared from 1-[6-[(1,3-dithia-2-cyclopentyl)-ethyl]-1,4-dioxaspiro[4,4]-none-7-yl]-3-(3-trifluoromethylphenoxy)-methyl]-trans-1-propene-3-one, the 1-[6-[(1,3-dithia-2-cyclopentyl)-ethyl]-1,4-dioxaspiro[4,4]-none-7-yl]-3-(3-trifluoromethylphenoxy)-methyl-trans-1-propene-3-ol.

I.R. 3500 cm$^{-1}$.
N.M.R. 5.3–5.7 ppm multiplett 2 H.

EXAMPLE 12 m

In a manner analogous to that described in Example 12 a, there was prepared from 1-[6-[(1,3-dithia-2-cyclopentyl)-ethyl]-1,4-dioxaspiro[4,4]-none-7-yl]-3-isobutyl-trans-1-propene-3-one, the 1-[6-[(1,3-dithia-2-cyclopentyl)-ethyl]-1,4-dioxaspiro[4,4]-none-7-yl]-3-isobutyl-trans-1-propene-3-ol.

I.R. 3500 cm$^{-1}$.
N.M.R. multiplett 2 H.

EXAMPLE 12 n

In a manner analogous to that described in Example 12 a, there was prepared from 1-[6[(1,3-dithia-2-cyclopentyl)-ethyl]-1,4-dioxaspiro[4,4]-none-7-yl]-3-(1,1-dimethylpentyl)-trans-1-propene-3-one, the 1-[6-[(1,3-dithia-2-cyclopentyl)-ethyl]-1,4-dioxaspiro[4,4]-none-7-yl]-3-(1,1-dimethylpentyl)-trans-1-propene-3-ol.

I.R. 3500 cm$^{-1}$.
N.M.R. 5.3–5.7 ppm multiplett 2 H.

EXAMPLE 13 a

1-[7-[(1,3-Dithia-2-cyclopentyl)]-3,3-dimethyl-1,5-dioxaspiro[5,4]-dec-8-yl]-trans-1-octene-3-ol-tetrahydropyranyl ether 1.1 g [2.5 moles] of 1-[7-[(1,3-dithia-2-cyclopentyl)-ethyl]-3,3-dimethyl-1,5-dioxaspiro[5,4]-dec-8-yl]-trans-1-octene-3-ol were dissolved in 20 ml of absolute ether, 20 mg of p-toluene-sulfonic acid were added, 1.2 ml [13 mmoles] of dihydropyrane in 10 ml of absolute ether were added dropwise and the whole was stirred for 4 hours at room temperature. 0.2 ml of dihydropyrane were again added. The reaction mixture was allowed to stand overnight and was then stirred for 30 minutes with 0.5 g of solid Na$_2$CO$_3$. The suspension was filtered, the filtrate was concentrated under reduced pressure and the oil that had formed was eluted with cyclohexane-ethyl acetate (9:1) over a silica gel column.

In the infrared spectrum, the analytically pure sample showed no OH-band at 3500 cm$^{-1}$.

Thin-layer chromatography R$_f$=0.64 on silica gel in cyclohexane/ether 4:6,
N.M.R. 4.5–4.8 ppm multiplett 2 H.

In analogous manner, there were prepared from the above-described alcohols the following tetrahydropyranyl ethers:

EXAMPLE 13 b

1-[7-[(1,3-Dithia-2-cyclopentyl)-ethyl]-3,3-dimethyl-1,5-dioxaspiro[5,4]-dec-8-yl]-trans-1-decene-3-ol-tetrahydropyranyl ether.

N.M.R. 4.5–4.8 ppm multiplett 2 H.

EXAMPLE 13 c

1-[7[(1,3-Dithia-2-cyclopentyl)-ethyl]-3,3-dimethyl-1,5-dioxaspiro[5,4]-dec-8-yl]-3-cyclohexyl-trans-1-propene-3-ol-tetrahydropyranyl ether.

N.M.R. 4.5–4.8 ppm multiplett 2 H.

EXAMPLE 13 d

1-[7-[(1,3-Dithia-2-cyclopentyl)-ethyl]-3,3-dimethyl-1,5-dioxaspiro[5,4]-dec-8-yl]-3-(1,1-dimethyl-3-oxapentyl)-trans-1-propene-3-ol-tetrahydropyranyl ether.

N.M.R. 4.5–4.8 ppm multiplett 2 H.

EXAMPLE 13 e

1-[7-[(1,3-Dithia-2-cyclopentyl)-ethyl]-3,3-dimethyl-1,5-dioxaspiro[5,4]-dec-8-yl]-3-cyclopentyl-trans-1-propene-3-ol-tetrahydropyranyl ether.

N.M.R. 4.5–4.8 ppm multiplett 2 H.

EXAMPLE 13 f

1-[7-[(1,3-Dithia-2-cyclopentyl)-ethyl]-3,3-dimethyl-1,5-dioxaspiro[5,4]-dec-8-yl]-trans-1-hexene-3-ol-tetrahydropyranyl ether.

N.M.R. 4.5–4.8 ppm multiplett 2 H.

EXAMPLE 13 g

From 1-[6-[(1,3-dithia-2-cyclopentyl)-ethyl]-1,4-dioxaspiro[4,4]-none-7-yl]-3-[1-methyl-1-[p-(p-chlorophenoxy)-phenoxy]-methyl-trans-1-propene-3-ol, the 1-[6-[(1,3-dithia-2-cyclopentyl)-ethyl]-1,4-dioxaspiro[4,4]-none-7-yl]-3-[1-methyl-1-[p-(p-chlorophenoxy)-phenoxy]-methyl]-trans-1-propene-3-ol-tetrahydropyranyl ether.

N.M.R. 4.1–5.0 ppm broad multiplett 4 H.

EXAMPLE 13 h

From the alcohol of Example 12 h, there was obtained in a manner analogous to that of Example 13 a the 1-[6-[(1,3-dithia-2-cyclopentyl)-ethyl]-1,4-dioxaspiro[4,4]-none-7-yl]-3-[1,1-dimethyl-1-[p-(p-chlorophenoxy)-phenoxy]-methyl]-trans-1-propene-3-ol-tetrahydropyranyl ether.

N.M.R. 4.5–4.8 ppm multiplett 2 H.

EXAMPLE 13 i

From the alcohol of Example 12 i, there was prepared in a manner analogous to that of Example 13 a the 1-[6-[(1,3-dithia-2-cyclopentyl)-ethyl]-1,4-dioxaspiro-[4,4]-none-7-yl]-3-phenoxymethyl-trans-1-propene-3-ol-tetrahydropyranyl ether.

N.M.R. 4.5–4.8 ppm multiplett 2 H.

EXAMPLE 13 j

From the alcohol of Example 12 j, there was prepared in a manner analogous to that of Example 13 a, the 1-[6[(1,3-dithia-2-cyclopentyl)-ethyl]-1,4-dioxaspiro[4,4]-none-7-yl]-3-(4-fluorophenoxy)-methyl-trans-1-propene-3-ol-tetrahydropyranyl ether.

N.M.R. 4.5–4.8 ppm multiplett 2 H.

EXAMPLE 13 k

From the alcohol of Example 12 k, there was prepared in a manner analogous to that of Example 13 a, the 1-[6-[(1,3-dithia-2-cyclopentyl)-ethyl]-1,4-dioxaspiro[4,4]-none-7-yl]-3-(3-chlorophenoxy)-methyl]-trans-1-propene-3-ol-tetrahydropyranyl ether.

N.M.R. 4.5–4.8 ppm multiplett 2 H.

EXAMPLE 13 l

From the alcohol of Example 12 l, there was prepared in a manner analogous to that of Example 13 a, the 1-[6-[(1,3-dithia-2-cyclopentyl)-ethyl]-1,4-dioxaspiro[4,4]-none-7-yl]-3-isobutyl-trans-1-propene-3-ol-tetrahydropyranyl ether.

N.M.R. 4.5–4.8 ppm multiplett 2 H.

EXAMPLE 13 m

From the alcohol of Example 12 m, there was obtained in a manner analogous to that of Example 13 a, the 1-[6-[(1,3-dithia-2-cyclopentyl)-ethyl]-1,4-dioxaspiro[4,4]-none-7-yl]-3-isobutyl-trans-1-propane-3-ol-tetrahydropyranyl ether.

N.M.R. 4.5–4.8 ppm multiplett 2 H.

EXAMPLE 13 n

From the alcohol of Example 12 n, there was prepared in a manner analogous to that of Example 13 a, the 1-[6-[(1,3-dithia-2-cyclopentyl)-ethyl]-1,4-dioxaspiro[4,4]-none-7-yl]-3-(1,1-dimethylpentyl)-trans-1-propene-3-ol-tetrahydropyranyl ether.

N.M.R. 4.5–4.8 ppm multiplett 2 H.

EXAMPLE 14 a

3-[3,3-Dimethyl-8[-3-pentyl-3-tetrahydropyranyloxy-trans-1-propenyl]-1,5-dioxaspiro[5,4]-dec-7-yl]-propionaldehyde 1.05 g [2.05 mmoles] of 1[7-[(1,3-dithia-2-cyclopentyl)]-3,3-dimethyl-1,5-dioxaspiro[5,4]-dec-8-yl]-trans-1-octene-3-ol-tetrahydropyranyl ether was stirred for 2 hours at 50° C. in 100 ml of DMF with 0.7 ml (10.3 mmoles) of methyl iodide, 1.4 g (14 moles) of $CaCO_3$ and 0.4 ml of $H_2O$. The solution was cooled, combined with 50 ml of acetone, filtered with suction to remove the precipitate and the filtrate was evaporated to dryness at 0.1 mm Hg. The residue was dissolved in ether, washed with $H_2O$, dried over $MgSO_4$ and the solvent was removed by distillation under reduced pressure. The oily residue which was not further purified showed in the infrared spectrum a strong carbonyl band at 1730 $cm^{-1}$.

Thin-layer chromatography $R_f$ value 0.51 on silica gel in cyclohexane/ether 4:6.

In analogous manner, there were obtained from the thioacetals 13 b–13 n, the following propionaldehydes of the general formula XX:

EXAMPLE 14 b

3-[3,3-dimethyl-8-[3-heptyl-3-tetrahydropyranyloxy-trans-1-propenyl]-1,5-dioxaspiro[5,4]-dec-7-yl]-propionaldehyde I.R. 1730 $cm^{-1}$.

EXAMPLE 14 c

3-[3,3-Dimethyl-8-[3-cyclohexyl-3-tetrahydropyranyloxy-trans-1-propenyl]-1,5-dioxaspiro[5,4]-dec-7-yl]-propionaldehyde I.R. 1730 $cm^{-1}$.

EXAMPLE 14 d

3-[3,3-Dimethyl-8-[3-(1,1-dimethyl-3-oxapentyl-3-tetrahydropyranyloxy-trans-1-propenyl]-1,5-dioxaspiro[5,4]-dec-7-yl]propionaldehyde.

I.R. 1730 $cm^{-1}$.

EXAMPLE 14 e

In a manner analogous to that described in Example 14 a, there was prepared from the tetrahydropyranyl ether of Example 13 e, the 3-[3,3-dimethyl-8-(3-cycloheptyl-3-tetrahydropyranyloxy-trans-1-propenyl)-1,5-dioxaspiro[5,4]-dec-7-yl]-propionaldehyde.

I.R. 1730 $cm^{-1}$.

EXAMPLE 14 f

In a manner analogous to that described in Example 14 a, there was prepared from the tetrahydropyranyl ether of Example 13 f, the 3-[3,3-dimethyl-8-(3-tetrahydropyranyloxy)-trans-1-hexenyl)1,5-dioxaspiro[5,4]-dec-7-yl]-propionaldehyde.

I.R. 1730 $cm^{-1}$.

EXAMPLE 14 g

In a manner analogous to that described in Example 14a, there was prepared from the tetrahydropyranyl ether of Example 13 g, the 3-[7-(3-tetrahydropyranyloxy)-3-[1-methyl-1-[p-(chlorophenoxy)phenoxy]-methyl]-[trans-1-propenyl]-1,4-dioxaspiro[4,4]-none-6-yl]propionaldehyde.

I.R. 1730 $cm^{-1}$.

EXAMPLE 14 h

In a manner analogous to that described in Example 14 a, there was prepared from the tetrahydropyranyl ether of Example 13 h, the 3-[7-(3-tetrahydropyranyloxy-3-[1,1-dimethyl-1-[p-(p-chlorophenoxy)-phenoxy]-methyl)-trans-1-propenyl]-1,4-dioxaspiro[4,4]none-6-yl]-propionaldehyde.

I.R. 1730 $cm^{-1}$.

EXAMPLE 14 i

In a manner analogous to that described in Example 14 a, there was prepared from the tetrahydropyranyl ether of Example 13 i, the 3-[7-(3-tetrahydropyranyloxy-3-phenoxymethyl-trans-1-propenyl)1,4-dioxaspiro[4,4]-none-6-yl]-propionaldehyde.

EXAMPLE 14 j

In a manner analogous to that described in Example 14 a, there was prepared from the tetrahydropyranyl ether of Example 13 j, the 3-[7-(3-tetrahydropyranyloxy-3-(4-fluorophenoxy)-methyl-trans-1- propenyl]-1,4-dioxaspiro[4,4]-none-6-yl]-propionaldehyde.
I.R. 1730 cm$^{-1}$.

EXAMPLE 14 k

In a manner analogous to that described in Example 14 a, there was prepared from the tetrahydropyranyl ether of Example 13 k, the 3-[7-(3-tetrahydropyranyloxy-3-(3-chlorophenoxy)-methyl-trans-1-propenyl)-1,4-dioxaspiro[4,4]-none-6-yl]-propionaldehyde.
I.R. 1730 cm$^{-1}$.

EXAMPLE 14 l

In a manner analogous to that described in Example 14 a, there was prepared from the tetrahydropyranyl ether of Example 13 l, the 3-[7-(3-tetrahydropyranyloxy-3-(3-trifluoromethylphenoxy)methyl-trans-1-propenyl)-1,4-dioxaspiro[4,4]-none-6-yl]-propionaldehyde.
I.R. 1730 cm$^{-1}$.

EXAMPLE 14 m

In a manner analogous to that described in Example 14 a, there was prepared from the tetrahydropyranyl ether of Example 13 m, the 3-[7-(3-tetrahydropyranyloxy-3-isobutyl-trans-1-propenyl)-1,4-dioxaspiro[4,4]-none-6-yl]-propionaldehyde.
I.R. 1730 cm$^{-1}$.

EXAMPLE 14 n

In a manner analogous to that described in Example 14 a, there was prepared from the tetrahydropyranyl ether of Example 13 n, the 3-[7-(3-tetrahydropyranyloxy-3-(1,1-dimethylpentyl)-trans-1-propenyl)]-1,4-dioxaspiro[4,4]-none-7-yl]-propionaldehyde.
I.R. 1730 cm$^{-1}$.

EXAMPLE 15 a

7-[3,3-Dimethyl-8-(3-pentyl-3-tetrahydropyranyloxy-trans-1-propenyl)-1,5-dioxaspiro[5,4]-dec-7-yl]-cis-4-heptenoic acid 0.3 g [10 moles] of 80% sodium hydride were heated for 1 hour under argon to 60°–65° C. in 3 ml of absolute dimethyl-sulfoxide and then 2.15 g [5 moles] of 4-carboxypropyltriphenylphosphonium bromide in 12 ml of DMSO were added. The solution whose color had change to red was stirred for 40 minutes at room temperature, and then 0.88 g of 2-[3,3-dimethyl-8-[3-pentyl-3-tetrahydropyranyloxy-trans-1-propenyl]-1,4-dioxaspiro[5-4]-dec-7-yl-propionaldehyde in 5 ml of DMSO was added dropwise. The solution was stirred for 16 hours at room temperature. It was diluted at 0° C. with 50 ml of ether, acidified to pH 1–2 with 5% NaHSO$_4$ solution, the organic phase was separated and the aqueous phase was extracted thrice with each time 75 ml of diethyl ether. The combined ether extracts were washed with water, dried over MgSO$_4$ and concentrated under reduced pressure.

The oil that had formed was chromatographed on silica gel and an analytically pure substance was obtained by elution with cyclohexane/ethyl acetate in a ratio of 8:2.

N.M.R. 8.5 ppm broad signal 1 H; 5.3–5.7 ppm broad signal 4 H; 4.7 ppm broad signal 1 H; 3.5 ppm duplett 4 H.

EXAMPLE 15 b

In analogous manner, there were obtained from the aldehydes of the general formula XX described in Examples 14 b–14 n, the following acids:
7-[3,3-dimethyl-8-[3-heptyl-3-tetrahydropyranyloxy-trans-1-propenyl]-1,5-dioxaspiro[5,4]-dec-7-yl]-cis-4-heptenoic acid.
N.M.R. 5.3–5.7 ppm broad signal 4 H.

EXAMPLE 15 c

7-[3,3-Dimethyl-8-[3-cyclohexyl-3-tetrahydropyranyloxy-trans-1-propenyl]-1,5-dioxaspiro[5,4]-dec-7-yl]-cis-4-heptenoic acid.
N.M.R. 5.3–5.7 ppm broad signal 4 H.

EXAMPLE 15 d

7-[3,3-Dimethyl-8-3-(1,1-dimethyl-3-oxa-pentyl)-3-tetrahydropyranyl-oxy-trans-1-propenyl]-1,5-dioxaspiro[5,4]-dec-7-yl]-cis-4-heptenoic acid.

EXAMPLE 15 e

In a manner analogous to that described in Example 15 a, there was obtained from the propionaldehyde of Example 14 e, the 7-[3,3-dimethyl-8-(3-cycloheptyl-3-tetrahydropyranyloxy-trans-1-propenyl)-1,5-dioxaspiro[5,4]-dec-7-yl]-cis-4-heptenoic acid.
N.M.R. 5.3–5.7 ppm broad signal 4 H.

EXAMPLE 15 f

In a manner analogous to that described in Example 15 a, there was prepared from the propionaldehyde of Example 14 f, the 7-[3,3-dimethyl-8-(3-tetrahydropyranyloxy-trans-1-hexenyl)1,5-dioxaspiro[5,4]-dec-7-yl]-cis-4-heptenoic acid.
N.M.R. 5.3 ppm broad signal 4 H.

EXAMPLE 15 g

In a manner analogous to that described in Example 15 a, there was obtained from the propionaldehyde of Example 14 g, the 7-[7-(3-tetrahydropyranyloxy-3-[1-methyl-[p- (p-chlorophenoxy)phenoxy]-methyl]-trans-1-propenyl)]-1,4-dioxaspiro[4,4]-none-6-yl]-cis-4-heptenoic acid.
N.M.R. 5.3–5.7 ppm broad signal 4 H.

EXAMPLE 15 h

In a manner analogous to that described in Example 15 a, there was obtained from the propionaldehyde of Example 14 h, the 7-[7-(3-tetrahydropyranyloxy-3-[1,1-dimethyl-[p-(p-chlorophenoxy)-phenoxy]-methyl]-trans-1-propenyl)]-1,4-dioxaspiro[4,4]-none-6-yl]-cis-4-heptenoic acid.
N.M.R. 5.3–5.7 ppm broad signal 4 H.

EXAMPLE 15 i

In a manner analogous to that described in Example 15 a, there was prepared from the propionaldehyde of Example 14 i, the 7-[7-(3-tetrahydropyranyloxy-3-phenoxymethyl-trans-1-propenyl)-1,4-dioxaspiro[4,4]-none-6-yl)-cis-4-heptenoic acid.
N.M.R. 5.3–5.7 ppm broad signal 4 H.

EXAMPLE 15 j

In a manner analogous to that described in Example 15 a, there was prepared from the propionaldehyde of Example 14 j, the 7-[7-(3-tetrahydropyranyloxy-3-(4- fluorophenoxy)-methyl-trans-1-propenyl)-1,4-dioxaspiro[4,4]-none-6-yl]-cis-4-heptenoic acid.

N.M.R. 5.3–5.7 ppm broad signal 4 H.

EXAMPLE 15 k

In a manner analogous to that described in Example 15 a, there was prepared from the propionaldehyde of Example 14 k, the 7-[7-(3-tetrahydropyranyloxy-3-(3-chlorophenoxy)-methyl-trans-1-propenyl)-1,4-dioxaspiro[4,4]-none-6-yl]-cis-4-heptenoic acid.

N.M.R. 5.3–5.7 ppm broad signal 4 H.

EXAMPLE 15 l

In a manner analogous to that described in Example 15 a, there was prepared from the propionaldehyde of Example 14 l, the 7-[7-(3-tetrahydropyranyloxy-3-(3-trifluoromethylphenoxy)methyl-trans-1-propenyl)-1,4-dioxaspiro[4,4]-none-6-yl]-cis-4-heptenoic acid.

N.M.R. 5.3–5.7 ppm broad signal 4 H.

EXAMPLE 15 m

In a manner analogous to that described in Example 15 a, there was prepared from the propionaldehyde of Example 14 m, the 7-[7-(3-tetrahydropyranyloxy-3-isobutyl-trans-1-propenyl)-1,4-dioxaspiro[4,4]-none-6-yl]-cis-4-heptenoic acid.

N.M.R. 5.3–5.7 ppm broad signal 4 H.

EXAMPLE 15 n

In a manner analogous to that described in Example 15 a, there was prepared from the propionaldehyde of Example 14 n, the 7-[7-(3-tetrahydropyranyloxy-3-(1,1-dimethylpentyl-trans-1-propenyl)-1,4-dioxaspiro[4,4]-none-7-yl]-cis-4-heptenoic acid.

N.M.R. 5.3–5.7 ppm broad signal 4 H.

EXAMPLE 16 a

7-[2-(3-Hydroxy-3-pentyl-trans-1-propenyl)-5-oxo-cyclopentyl]-cis-4-heptenoic acid.

0.41 g [1 mmole] of 7-[3,3-dimethyl-8-(3-pentyl-3-tetrahydropyranyloxy-trans-1-propenyl)-1,5-dioxas-piro[5,4]-dec-7-yl]-cis-4-heptenoic acid was dissolved in 25 ml of ethyl alcohol and stirred with 5 ml of 2% aqueous oxalic acid solution for 20 hours at room temperature under nitrogen. The solvent was partially removed by distillation under reduced pressure, the residue was combined with 20 ml of a saturated NaCl solution and extracted twice with 100 ml of diethyl ether. The combined ether extracts were washed thrice with each time 20 ml of $H_2O$, dried and concentrated.

337 mg of a light oil were obtained: 7-[3,3-dimethyl-8-(3-pentyl-3-hydroxy-trans-1-propenyl)]-1,5-dioxas-piro[5,4]-dec-7-yl)-cis-4-heptenoic acid.

These 337 mg from the first stage were stirred in 30 ml of acetone with 20 mg of p-toluene-sulfonic acid monohydrate for 5 hours at 50° C. under nitrogen and allowed to stand overnight at room temperature. The mixture was then concentrated, the residue was dissolved in ether, washed with water and concentrated. The residue was chromatographed on silica gel and the analytically pure substances were obtained by elution with a solvent mixture of 80 parts of cyclohexane, 20 parts of ethyl acetate and 1 part of glacial acetic acid. 2 Isomers were isolated which were found to distinguish in their $R_f$-values on silica gel (of Messrs. Merck) in the solvent mixture cyclohexane/ethylacetate/glacial acetic acid 80/20/1 as follows:

isomer B 0.41.
isomer A 0.36.

After HD exchange, the N.M.R. spectrum of both isomers was practically identical.

Before HD exchange:
5.2–6.0 ppm broad signal 6 H.
4.05 ppm broad signal 1 H.

After HD exchange:
5.2–5.4 ppm broad signal 2 H.
5.5–5.7 ppm broad signal 2 H.
4.05 ppm broad signal 1 H.

In analogous manner, there were prepared from compounds of the general formula XXI, as those described in Example 15 b–15 n, the following carboxylic acids of the general formula I, in which $R_1$ and $R_2$ together represent oxygen:

EXAMPLE 16 b

7-[2-(3-hydroxy-3-heptyl-trans-1-propenyl)-5-oxo-cyclopentyl]-cis-4-heptenoic acid.

N.M.R. 5.2–6.0 ppm broad signal 6 H.

EXAMPLE 16 c

7-[2-(3-Hydroxy-3-cyclohexyl-trans-1-propenyl)-5-oxocyclopentyl]-cis-4-heptenoic acid.

N.M.R. 5.2–6.5 ppm broad signal 6 H.

EXAMPLE 16 d

7-[2-[3-Hydroxy-3-(1,1-dimethyl-3-oxa-pentyl)-trans-1propenyl]-5oxo-cyclopentyl]-cis-4-heptenoic acid.

N.M.R. 5.2–6.0 ppm broad signal 6 H.

EXAMPLE 16 e

In a manner analogous to that described in Example 16 a, there was prepared from the heptenoic acid of Example 15 e, the 7-[2-(3-hydroxy-3-cycloheptyl-trans-1-propenyl)-5-oxocyclopentyl]-cis-4-heptenoic acid.

N.M.R. 5.2–6.2 ppm broad signal 6 H.

EXAMPLE 16 f

In a manner analogous to that described in Example 16 a, there was prepared from the heptenoic acid of Example 15 e, the 7-[2-(3-hydroxy-trans-1-hexenyl)-5-oxycyclopentyl]-cis-4-heptenoic acid.

N.M.R. 5.2–6.5 ppm broad signal 6 H.

EXAMPLE 16 g

In a manner analogous to that described in Example 16 a, there was prepared from the heptenoic acid of Example 15 g, the 7-[2-(3-hydroxy-3-[1-methyl-[p-(p-chlorophenoxy)-phenoxy]methyl-trans-1-propenyl)-5-oxocyclopentyl]-cis-4-heptenoic acid.

N.M.R. 5.2–6.1 ppm broad signal 6 H.

EXAMPLE 16 h

In a manner analogous to that described in Example 16 a, there was prepared from the heptenoic acid of Example 15 h, the 7-[2-[3-hydroxy-3-[1,1-dimethyl-1-[p-(p-chlorophenoxy)phenoxy]-methyl]-trans-1-propenyl]-5-oxocyclopentyl]-cis-4-heptenoic acid.

N.M.R. 5.2–6.0 ppm broad signal.

EXAMPLE 16 i

In a manner analogous to that described in Example 16 a, there was prepared from the heptenoic acid of Example 15 i, the 7-[2-(3-hydroxy-3-phenoxymethyl-trans-1-propenyl)-5-oxocyclopentyl]-cis-4-heptenoic acid.

N.M.R. 5.2–6.1 ppm broad signal 6 H.

EXAMPLE 16 j

In a manner analogous to that described in Example 16 a, there was prepared from the heptenoic acid of Example 15 j, the 7-[2-[3-hydroxy-3-(4-fluorophenoxy)-methyl-trans-1-propenyl]-5-oxocyclopentyl]-cis-4-heptenoic acid.

N.M.R. 5.2–6.5 ppm broad signal 6 H.

EXAMPLE 16 k

In a manner analogous to that described in Example 16 a, there was prepared from the heptenoic acid of Example 15 k, the 7-[2-[3-hydroxy-3-(3-chlorophenoxy)-methyl-trans-1-propenyl]-5-oxocyclopentyl]-cis-4-heptenoic acid.

N.M.R. 5.2–6.0 ppm broad signal 6 H.

EXAMPLE 16 l

In a manner analogous to that described in Example 16 a, there was prepared from the heptenoic acid of Example 15 l, the 7-[2-[3-hydroxy-3-(3-trifluoromethylphenoxy)-methyl-trans-1-propenyl]-5-oxocyclopentyl]-cis-4-heptenoic acid.

N.M.R. 5.2–6.3 ppm.

EXAMPLE 16 m

In a manner analogous to that described in Example 16 a, there was prepared from the heptenoic acid of Example 15 m, the 7-[2-(3-hydroxy-3-isobutyl-trans-1-propenyl)-5-oxocyclopentyl]-cis-4-heptenoic acid.

N.M.R. 5.2–6.1 ppm broad signal.

EXAMPLE 16 n

In a manner analogous to that described in Example 16 a, there was prepared from the heptenoic acid of Example 15 n, the 7-[2-[3-hydroxy-3-(1,1-dimethylpentyl)-trans-1-propenyl]-5-oxocyclopentyl]-cis-4-heptenoic acid.

N.M.R. 5.2–6.5 broad signal 6 H.

EXAMPLE 17 a

7-[2-(3-Hydroxy-3-pentyl-trans-1-propenyl)-5-hydroxycyclopentyl]-cis-4-heptenoic acid 150 mg of 7-[2-(3-hydroxy-3-pentyl-trans-1-propenyl)-5-oxocyclopentyl]-cis-4-heptenoic acid were dissolved in 20 ml of methanol and three times each time 150 mg of $NaBH_4$ were added within the course 1½ hours. The reaction solution was adjusted to pH 7 by means of glacial acetic acid, the solvent was removed by distillation under reduced pressure, the residue was acidified with 2N-HCl to pH 1 and extracted thrice with 150 ml of ether. After washing, the organic phase was concentrated.

I.R. 3500 $cm^{-1}$; 1720–1700 $cm^{-1}$.

In analogous manner, there were prepared from the carboxylic acids of the general formula I, in which $R_1$ and $R_2$ together represent oxygen and which are described in Examples 16 b–16 d, carboxylic acids of the general formula I, in which $R_1$ and $R_2$ each represent hydrogen or the hydroxyl group:

EXAMPLE 17 b

7-[2-(3-Hydroxy-3-heptyl-trans-1-propenyl)-5-hydroxy-cyclopentyl]-cis-4-heptenoic acid.

I.R. 3500 $cm^{-1}$; 1720–1700 $cm^{-1}$.

EXAMPLE 17 c

7-[2-(3-Hydroxy-3-cyclohexyl-trans-1-propenyl)-5-hydroxycyclopentyl]-cis-4-heptenoic acid.

I.R. 3500 $cm^{-1}$; 1720–1700 $cm^{-1}$.

EXAMPLE 17 d

7-[2-[3-Hydroxy-3-(1,1-dimethyl-3-oxa-pentyl)-trans-1-propenyl]-5-hydroxy-cyclopentyl]-cis-4-heptenoic acid.

I.R. 3500 $cm^{-1}$; 1720–1700 $cm^{-1}$.

EXAMPLE 17 e

7-[2-(3-Hydroxy-3-cycloheptyl-trans-1-propenyl)-5-hydroxycyclopentyl]-cis-4-heptenoic acid.

I.R. 3500 $cm^{-1}$; 1720–1700 $cm^{-1}$.

EXAMPLE 17 f

7-[2-(3-Hydroxy-trans-1-hexenyl)-5-hydroxy-cyclopentyl]-cis-4-heptenoic acid.

I.R. 3500 $cm^{-1}$; 1720–1700 $cm^{-1}$.

EXAMPLE 17 g

7-[2-[3-Hydroxy-3-[1-methyl-[p-(p-chlorophenoxy)-phenoxy]methyl]-trans-1-propenyl]-5-hydroxy-cyclopentyl]-cis-4-heptenoic acid.

I.R. 3500 $cm^{-1}$; 1720–1700 $cm^{-1}$.

EXAMPLE 17 h

7-[2-[3-Hydroxy-3-[1,1-dimethyl-1-[4-(4-chlorophenoxy)-phenoxy]-methyl]-trans-1-propenyl]-5-hydroxy-cyclopentyl]-cis-4-heptenoic acid.

I.R. 3500 $cm^{-1}$; 1720–1700 $cm^{-1}$.

EXAMPLE 17 i

7-[2-(3-Hydroxy-3-phenoxymethyl-trans-1-propenyl)-5-hydroxycyclopentyl]-cis-4-heptenoic acid.

I.R. 3500 $cm^{-1}$; 1720–1700 $cm^{-1}$.

EXAMPLE 17 j

7-[2-[3-Hydroxy-3-(4-fluorophenoxy-)-methyl-trans-1-propenyl]-5-hydroxy-cyclopentyl]-cis-4-heptenoic acid.

I.R. 3500 $cm^{-1}$; 1720–1700 $cm^{-1}$.

EXAMPLE 17 k

7-[2-[3-Hydroxy-3-(3-chlorophenoxy)-methyl-trans-1-propenyl]-5-hydroxy-cyclopentyl]-cis-4-heptenoic acid.

I.R. 3500 $cm^{-1}$; 1720–1700 $cm^{-1}$.

EXAMPLE 17 l

7-[2-[3-Hydroxy-3-(3-trifluoromethylphenoxy)-methyl-trans-1-propenyl]-5-hydroxy-cyclopentyl]-cis-4-heptenoic acid.

I.R. 3500 $cm^{-1}$; 1720–1700 $cm^{-1}$.

EXAMPLE 17 m

7-[2-[3-Hydroxy-3-isobutyl-trans-1-propenyl]-5-hydroxycyclopentyl]-cis-4-heptenoic acid.

I.R. 3500 $cm^{-1}$; 1720–1700 $cm^{-1}$.

EXAMPLE 17 n

7-[2-[3-Hydroxy-3-hydroxy-3-(1,1-dimethylpentyl)-trans-1-propenyl]-5-hydroxycyclopentyl]-cis-4-heptenoic acid I.R. 3500 $cm^{-1}$; 1720–1700 $cm^{-1}$.

EXAMPLE 18

The isomer A and the isomer B of 7-[2-(3-hydroxy-3-pentyltrans-1-propenyl)-5-oxo-cyclopentyl]-cis-4-heptenoic acid (Example 16 a) were mixed in a weight proportion of 1:1, dissolved in ethyl alcohol, diluted with distilled water and atomized at a total volume of 0.02 ml per minute in an ultrasonic atomizer.

For testing the broncho-spasmolytic activity, the measurement of the breath volume according to Konzett and Rossler (Arch. exp. Path. Pharmakol. 195, 71 (1940)) was used. As test animals, male white Guinea pigs having a weight of 400–500 g were used which had been anesthetized with 10 mg/kg i.p. of Evipan and 200 mg/kg. i.p. of urethane.

As asthmogenic substance, histamine-dihydrochloride in a dose of 1–5 ug/kg was administered. The experimental data were subjected to a regression analysis and the equation of the regression line $Y = A + B \cdot / g(X)$ was calculated. Therewith, also the average inhibition dose ($ED_{50}$) as the dose which inhibits the asthmogenic action by 50% of its initial value, could be determined.

Results

7-[2-(3-Hydroxy-3-pentyl-trans-1-propenyl)-5-oxo-cyclopentyl]-cis-4-heptenoic acid.

|  | Average inhibition dose | |
|---|---|---|
|  | i.v. ($\mu$g/kg) | Aerosol ($\mu$g/animal) |
| Isomer A | 0.08 | 0.01 |
| Isomer B | 0.1 | 0.1 |
| Mixture A + B (1:1) | 0.1 | 0.002 |

We claim:
1. A compound of the formula

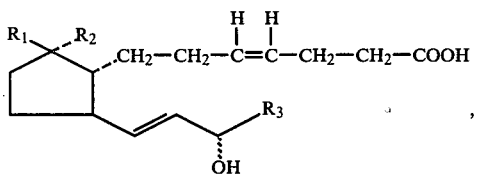

physiologically tolerated salts thereof with organic and inorganic bases, and esters thereof with aliphatic, cycloaliphatic, or araliphatic alcohols of 1 to 8 carbon atoms, wherein $R_1$ and $R_2$, taken alone, are different and are each hydrogen or hydroxy;

$R_1$ and $R_2$, taken together, are oxygen; and $R_3$ is straight chain or branched alkyl having 1 to 10 carbon atoms substituted by O-aryl or O-benzyl, which themselves may be substituted by one or several halogen atoms, by trifluoromethyl, by alkyl having 1 to 3 carbon atoms, by phenoxy, or by phenoxy substituted by one or several halogen atoms.

2. A compound as in claim 1 wherein $R_1$ and $R_2$ together are oxygen.